(12) United States Patent
Cool

(10) Patent No.: US 6,912,469 B1
(45) Date of Patent: Jun. 28, 2005

(54) ELECTRONIC HYBRIDIZATION ASSAY AND SEQUENCE ANALYSIS

(76) Inventor: Kenneth J. Cool, 378 Inverness Trail, Dakota Dunes, SD (US) 57049

( * ) Notice: Subject to any disclaimer, the term of this patent is extended or adjusted under 35 U.S.C. 154(b) by 202 days.

(21) Appl. No.: 09/846,985

(22) Filed: May 1, 2001

Related U.S. Application Data
(60) Provisional application No. 60/201,930, filed on May 5, 2000.

(51) Int. Cl.⁷ .................. G06F 19/00; G11C 17/00; G05B 15/00
(52) U.S. Cl. ...................... 702/19; 364/94; 700/1
(58) Field of Search ........................... 702/19; 364/94; 700/1

(56) References Cited

U.S. PATENT DOCUMENTS

| | | | |
|---|---|---|---|
| 3,670,151 A | | 6/1972 | Lindsay et al. |
| 4,660,164 A | * | 4/1987 | Leibowitz |
| 4,729,947 A | | 3/1988 | Middendorf et al. |
| 5,077,753 A | | 12/1991 | Grau, Jr. et al. |
| 5,207,880 A | | 5/1993 | Middendorf et al. |
| 5,549,805 A | | 8/1996 | Middendorf et al. |
| 5,556,749 A | * | 9/1996 | Mitsuhashi et al. ............ 435/6 |
| 5,650,785 A | | 7/1997 | Rodal |
| 5,784,422 A | | 7/1998 | Heermann |
| 5,794,068 A | | 8/1998 | Asghar et al. |
| 5,809,060 A | | 9/1998 | Cafarella et al. |
| 5,849,486 A | * | 12/1998 | Heller et al. ................... 435/6 |
| 5,862,231 A | | 1/1999 | Tokuhisa |
| 5,871,697 A | * | 2/1999 | Rothberg et al. .......... 422/68.1 |
| 5,925,525 A | * | 7/1999 | Fodor et al. ................... 435/6 |
| 6,021,421 A | | 2/2000 | Retter et al. |
| 6,075,812 A | | 6/2000 | Cafarella et al. |

FOREIGN PATENT DOCUMENTS

| GB | WO 99/01940 | * | 1/1999 |
|---|---|---|---|
| WO | WO 99/01940 | | 1/1999 |

OTHER PUBLICATIONS

Donald C. Benson, Digital signal processing methods for biosequence comparison, Apr. 1990, Nucleic Acids Research, vol. 18, No. 10, pp. 3001–3006.*

Altschul et al, Gapped BLAST and PSI–BLAST: a new generation of protein database search programs, Jul. 1997, Nucleic Acids Research, vol. 25, No. 17, pp. 3389–3402.*

Ashley W. Gary, "Modeling, Synthesis, and Hybridization Properties of (L)–Ribonucleac Acid", J.Am.Chem.Soc., 1992, vol. 114, No. 25, pp. 9731–9736.*

Ashley, "Modleing, Synthesis, and Hybridization Properties of (L)–Ribonucleic Acid", J.Am. Chem.Soc., 1992, pp. 9731–9736, vol. 114, No. 25, American Chemical Society, USA.

Benson, "Digital Signal Processing Methods for Biosequence Comparsion", Nucleic Acids Research, 1990, pp. 3001–3306, vol. 18, No. 10, Oxford University Press, USA.

Altschul et al., "Gapped BLAST and PSI–BLAST: A New Generation of Protein Database Search Programs", Nucleid Acids Research, 1997, pp. 3389–3402, vol. 25, No. 17, USA.

Proakis and Manolakis, "Introduction to Digital Signal Processing", 1988, pp. 111–129, Macmillan Publishing Company, New York, USA.

Adren et al., "CCK Modulation Delivers 11Mbps for High Rate IEEE 802.11 Extension", Wireless Symposium/Portable by Design Conference, 1999, Palm Bay, FL, USA.

* cited by examiner

*Primary Examiner*—John S. Brusca
(74) *Attorney, Agent, or Firm*—Kenneth J. Cool

(57) ABSTRACT

An electronic hybridization assay implements a hybridization reaction, or a sequence analysis, on sequences representative of the sequences of the molecules under examination to provide an output representative of a chemical hybridization reaction. An electronic hybridization machine implements a correlation algorithm where the correlation output provides information regarding the relationship between the molecules under examination. In one aspect, the degree of similarity between the molecules is indicated by the correlation output value. In another aspect, a locus of similarity between the molecules is indicated by a maximum value in the correlation output sequence. In a particular aspect, the sequences are encoded in an optimized format to optimize the operation of the operation of the electronic hybridization machine.

16 Claims, 7 Drawing Sheets

ELECTRONIC HYBRIDIZATION ASSAY AND SEQUENCE ANALYSIS

CROSS-REFERENCE TO RELATED APPLICATION

The present application claims the benefit under 35 U.S.C. § 119(e) to provisional patent application No. 60/201,930 filed May 5, 2000.

BRIEF DESCRIPTION OF THE DRAWINGS

The numerous advantages of the present invention may be understood by those skilled in the art by reference to the accompanying figures in which.

DETAILED DESCRIPTION

Figure 1:
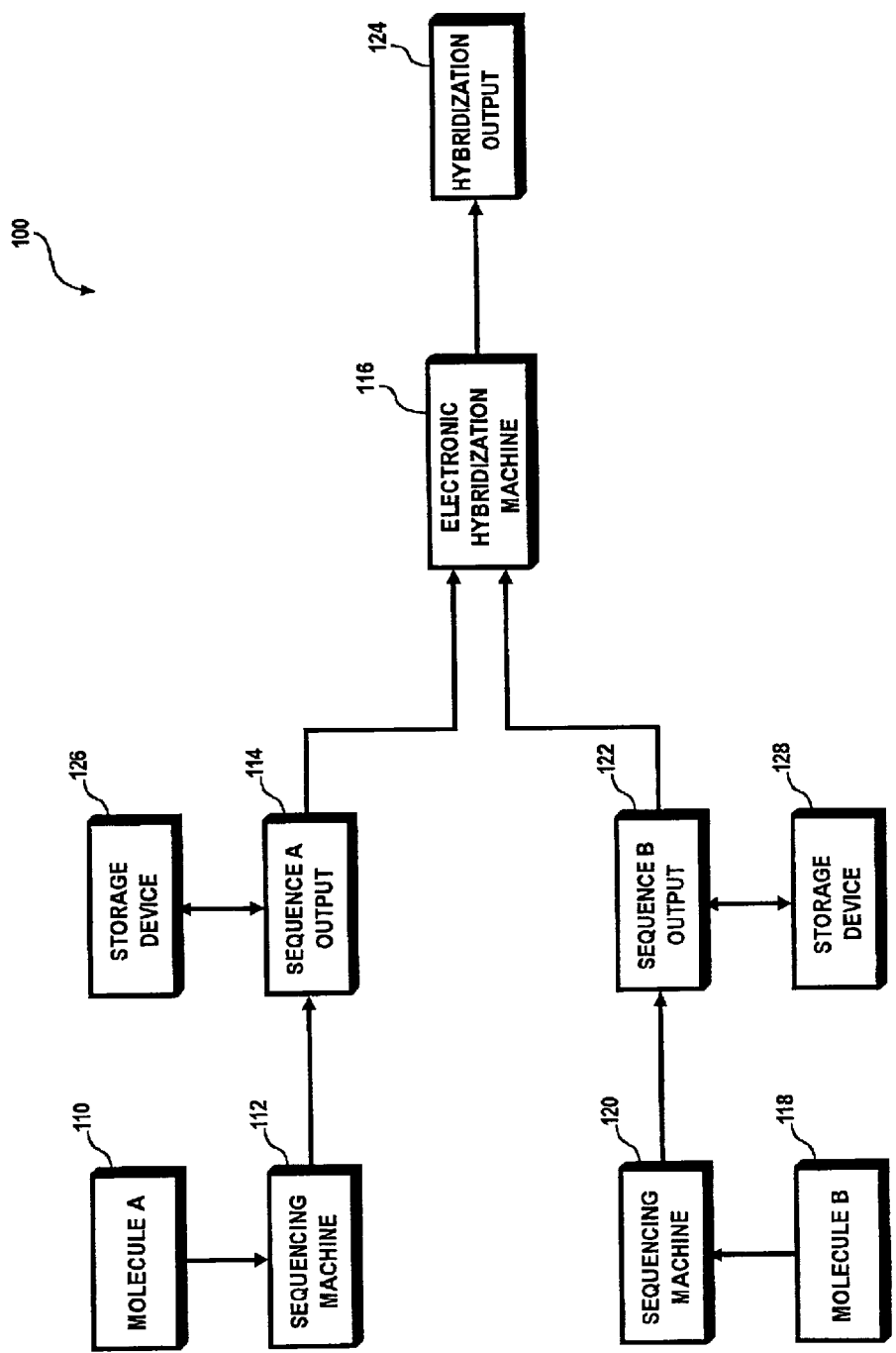
FIG. 1 is a block diagram of an electronic hybridization system in accordance with the present invention.

Referring now to FIG. 1, a block diagram of a system for implementing an electronic hybridization assay in accordance with the present invention will be discussed. In operation of hybridization system 100, a first molecule (MOLECULE A) 110 is provided to a sequencing machine (SEQUENCING MACHINE) 112. Sequencing machine 112 determines the sequence of the particular molecular components or residues, referred to generally as subunits, of first molecule 110. For example, first molecule 110 in one embodiment is an oligonucleotide molecule such as DNA or RNA that has a sequence determined by the linear order of its component bases. Such a DNA molecule may comprise, for example, three bases where the molecule is single stranded, or may comprise six base pairs, respectively, where the molecule is double stranded, in which case first molecule 110 has an adenine (A), guanine (G), and a thymine (T) base in sequence. Cytosine (C) may also be one of the bases of a DNA molecule. Thus, where first molecule 110 is a single stranded molecule, it may have N number of residues where or subunits where N may range from one to infinity, or may have 2N number of residues or subunits, where first molecule 110 is double stranded. Where first molecule 110 is an RNA oligonucleotide, it may include the base uracil (U) instead of thymine. When first molecule 110 is sequenced by sequencing machine 112, sequencing machine 112 provides an output sequence (SEQUENCE A OUTPUT) 114 that is representative of the sequence of the residues, or subunits, of first molecule 110. Sequence output 114 of sequencing machine 112 is provided as an input to an electronic hybridization machine (ELECTRONIC HYBRIDIZATION MACHINE) 116 which is capable of reading and interpreting sequence output 114. In a likewise manner, a second molecule (MOLECULE B) 118 is sequenced by sequencing machine (SEQUENCING MACHINE) 120, which provides a sequence output (SEQUENCE OUTPUT) 122 that is representative of the sequence of second molecule 118. Second molecule 118 may be an oligonucleotide similar to first molecule 110 (e.g., DNA or RNA). Sequence output 122 of sequencing machine 120 is provided to electronic hybridization machine 116 so that an electronic hybridization reaction between first molecule 110 and second molecule 118 is performed electronically rather than chemically. The electronic hybridization reaction, generally referred to as a sequence analysis, performed by electronic hybridization machine 116 is in one embodiment of the invention representative of an actual chemical reaction between the physical forms of first molecule 110 and second molecule 118. In a physical world chemical hybridization reaction between first molecule 110 and second molecule 118, the extent to which the two molecules bind to one another is typically indicated with a reporter molecule such as a radioactive of fluorescent reporter molecule. The greater the similarity between the two molecules the greater the amount of binding between the two chemicals, resulting in a fluorescent or radioactive intensity of a signal provided by the reporter molecule. The intensity of the reporter molecule is usually observed by the human eye, or by a detector sensitive to the fluorescence or radioactivity of the reporter molecule. With the present invention, such a hybridization reaction is modeled electronically, in the electronic domain, by electronic hybridization machine 116, which produces a hybridization output (HYBRIDIZATION OUTPUT) 124 representative of information resulting from a hybridization reaction between first molecule 110 and second molecule 118. The invention is not intended to be limited to hybridization reactions, which are described herein for purposes of illustration. The invention may be expanded or adapted to other types of sequence analysis reactions in accordance with the present invention as described herein.

Hybridization assays in the chemical domain are executed using a chemical reaction between two molecules to determine a relationship between the molecules that depends on the level of binding between the two molecules. The level of binding is indicative of the similarity between the two molecules. Hybridization assays are used, for example, to identify the sequence of a test molecule such as an oligonucleotide by determining whether and to what extent the test molecule will bind with one or more known reference molecules. Hybridization assays are executed in the chemical domain using an actual chemical reaction to determine the relationship between a test molecule and one or more target molecules. The hybridization assay provides information such as the identity of an unknown molecule, the sequence similarity between two molecules, and genetic homology.

Molecular hybridization is a method for identifying nucleic acid molecules and the degree to which the molecules are related in base sequence to a labeled nucleic acid probe. In molecular hybridization, single stranded nucleic acids molecules are combined and allowed to anneal. One of the molecules is a labeled probe molecule, and another of the molecules is a target molecule. In the event the nucleic acid molecules are double-stranded, the strands are separated into single-stranded form prior to executing the assay. The single-stranded molecules are combined and allowed to anneal by binding at complementary base sequences. Hybridization is the binding between the probe molecules and the target molecules. Whether, where, and to what extent the probe molecule binds with the target molecule can be detected with a detector that is responsive to the label, typically a fluorescent or radioactive molecule. Information concerning the identity of and the relationship between probe and target molecules is provided by the resulting binding pattern observed in the hybridization reaction. In one aspect, sequences in the target molecule that are related to the probe molecule can be identified. Conversely, an unknown or known probe molecule can be hybridized with a group of target molecules having known sequence and genetic origin to identify the probe molecules by determining which of the known target molecule strands that the probe molecule hybridizes with, or by comparing the similarity of the probe molecule with one or more target molecule strands, for example to determine homology. Such converse hybridization assays are typically implemented using microarrays, or gene chips. Hybridization assays may be performed using DNA-DNA, RNA-RNA and RNA-DNA reactions. These reactions are implemented in the chemical domain.

In addition, information may be determined from biological and similar molecules based upon corresponding molecules that the biological molecules code for. For example, if a base sequence, or partial sequence, of a nucleotide molecule is known, then a complementary nucleotide sequence can be determined based upon Watson-Crick base pairing rules. Thus, in one embodiment, a nucleotide molecule codes for its Watson-Crick complementary sequence so that electronic hybridization machine 116 can code, decode, and compare sequences accordingly. In another embodiment, a nucleotide sequence can encode a corresponding amino acid sequence according to the biological operation of a ribosome during peptide and protein synthesis. Thus, a three nucleotide base sequence defines a codon that codes for a corresponding amino acid. Electronic hybridization machine 116 is able to encode, decode, and compares sequences accordingly. For example, if a peptide or a protein sequence is known, electronic hybridization machine 116 compares the amino acid reside sequence of the peptide or protein to a nucleotide sequence, such as a DNA sequence, to determine whether a sequence of the DNA is likely to code for that peptide or protein in accordance with the present invention. In one particular embodiment, the nucleotide sequence is converted into a corresponding protein sequence electronically using biological codon rules, and the two protein sequences are compared electronically with electronic hybridization machine 116. In another embodiment, the protein sequence is converted into a corresponding nucleotide sequence electronically using biological codon rules, and the two nucleotide sequences are compared with electronic hybridization machine 116. Since an amino acid may be coded by multiple nucleotide triplets (codons), for example due to wobble in the biological code, this may be accounted for, for example, by selecting corresponding nucleotide triplets according to frequency or likelihood of occurrence. In a particular embodiment, multiple proposed nucleotide sequences can be executed by electronic hybridization machine 116, or a nucleotide in a wobble position can be designated generically as one, two, or more candidate nucleotides. In this sense of the above examples, electronic hybridization machine 116 is capable of performing sequence analysis between two molecules in the electronic domain that is practical, if not impossible, to implement in the chemical domain, for example comparing a protein sequence to a nucleotide sequence in a hybridization-like assay. Thus, the term hybridization assay is not limited to just the corresponding reactions in the chemical domain, and encompasses far many other types of reactions, and thus includes any sequence analysis. The sequences capable of being analyzed by electronic hybridization machine 116 may be any suitable biological sequence discussed herein or apparent there from. Furthermore, any other suitable molecule, sequence, or signal may be likewise analyzed by electronic hybridization machine 116. A non-exhaustive list of such molecules includes any DNA molecule, any RNA molecule, any peptide, any protein, any amino acid, or any hybrid, conformation, combination, or derivative thereof. Likewise, a non-exhaustive list of a sequence includes the underlying information encoded or represented by any DNA molecule, any RNA molecule, any peptide, any protein, any amino acid, or any hybrid, conformation, combination, or derivative thereof, and so on. Other molecular sequences, biological or otherwise, are also contemplated as being adaptable to analysis according to the present invention.

The invention provides the capability to implement a molecular hybridization reaction assay or the like without requiring an actual chemical reaction. The hybridization reaction is effectively implemented by a machine such as a computer, a hardware device, or a digital signal processor to provide the speed, flexibility, and capability of repetition of the same assay without requiring new materials to execute the assay. The invention may be implemented with a general purpose computer system or a hardware device, and in addition, the invention provides also the capability to take advantage of digital signal processing techniques to increase the speed of the assays while providing the flexibility of a general purpose computer system. In accordance with one aspect of the invention, a method and apparatus are provided by which a molecular sequence may be encoded into a format that optimizes the speed and efficiency at which the information may be electronically processed, by a general purpose computer, by a hardware device, by a digital signal processor, or by other types of electronic machines. In accordance with one aspect of the present invention, an electronic hybridization machine executes a correlation algorithm to perform a hybridization assay. The functions of an electronic hybridization machine and the execution of a correlation algorithm or the like is discussed herein.

Figure 2:
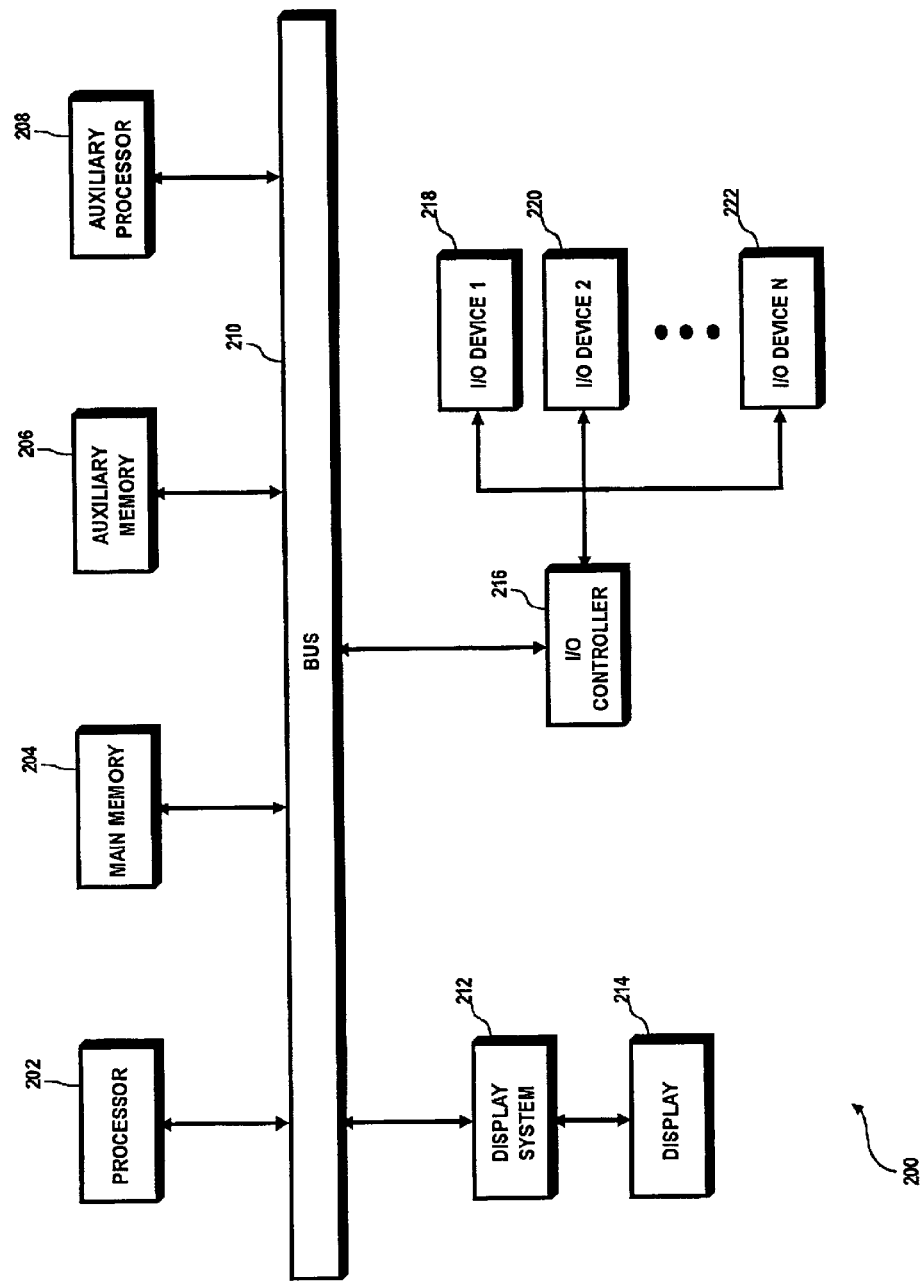
FIG. 2 is a block diagram of a computer appliance operable to embody the present invention.

Referring now to FIG. 2, a computer appliance in accordance with the present invention is shown. The computer appliance shown in FIG. 2 is generally representative of the architecture of a computer system embodiment of the present invention. Computer system 200 may be configured to implement hybridization system 100 of FIG. 1, for example, by implementing electronic hybridization machine 116. A central processor 202 controls computer system 200. Central processor 202 includes a central processing unit such as a microprocessor or microcontroller for executing programs, performing data manipulations and controlling the tasks of computer system 200. Communication with central processor 202 is implemented through a system bus 210 for transferring information among the components of computer system 200. Bus 210 may include a data channel for facilitating information transfer between storage and other peripheral components of computer system 200. Bus 210 further provides the set of signals required for communication with central processor 202 including a data bus, address bus, and control bus. Bus 210 may comprise any state of the art bus architecture according to promulgated standards, for example industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and so on. Furthermore, bus 210 may be compliant with any promulgated industry standard. For example, bus 210 may be designed in compliance with any of the following bus architectures: Industry Standard Architecture (ISA), Extended Industry Standard Architecture (EISA), Micro Channel Architecture, Peripheral Component Interconnect (PCI), Universal Serial Bus (USB), Access.bus, IEEE P1394, Apple Desktop Bus (ADB), Concentration Highway Interface (CHI), Fire Wire, Geo Port, or Small Computer Systems Interface (SCSI), for example.

Other components of computer system 200 include main memory 204, auxiliary memory 206, and an auxiliary processor 208 as required. Main memory 204 provides storage of instructions and data for programs executing on central processor 202. Main memory 204 is typically semiconductor based memory such as dynamic random access memory (DRAM) or static random access memory (SRAM). Auxiliary memory 206 provides storage of instructions and data that are loaded into the main memory 204 before execution. Auxiliary memory 206 may include semiconductor based memory such as read-only memory (ROM), programmable read-only memory (PROM) erasable programmable read-only memory (EPROM), electrically erasable read-only memory (EEPROM), or flash memory (block oriented memory similar to EEPROM). Auxiliary memory 206 may also include a variety of non-semiconductor based memories, including but not limited to magnetic tape, drum, floppy disk, hard disk, optical, laser disk, compact disc read-only memory (CD-ROM), digital versatile disk read-only memory (DVD-ROM), digital versatile disk random-access memory (DVD-RAM), etc. Other varieties of memory devices are contemplated as well. In general and accordance with the present invention, a memory device such as referred to herein may be generally described as a machine readable medium. Computer system 200 may optionally include an auxiliary processor 208 which may be a digital signal processor (a special-purpose microprocessor having an architecture suitable for fast execution of signal processing algorithms), a back-end processor (a slave processor subordinate to the main processing system), an additional microprocessor or controller for dual or multiple processor systems, or a coprocessor.

Computer system 200 further includes a display system 212 for connecting to a display device 214, and an input/output (I/O) system 216 for connecting to one or more I/O devices 218, 220, up to N number of I/O devices 222. Display system 212 may comprise a video display adapter having all of the components for driving the display device, including video random access memory (VRAM), buffer, and graphics engine as desired. Display device 214 may comprise a cathode ray-tube (CRT) type display such as a monitor or television, or may comprise alternative type of display technologies such as a liquid-crystal display (LCD), a light-emitting diode (LED) display, or a gas or plasma display. Input/output system 216 may comprise one or more controllers or adapters for providing interface functions between one or more of I/O devices 218–222. For example, input/output system 216 may comprise a serial port, parallel port, infrared port, network adapter, printer adapter, radio-frequency (RF) communications adapter, universal asynchronous receiver-transmitter (UART) port, etc., for interfacing between corresponding I/O devices such as a mouse, joystick, trackball, track pad, track stick, infrared transducers, printer, modem, RF modem, bar code reader, charge-coupled device (CCD) reader, scanner, compact disc (CD), compact disc read-only memory (CD-ROM), digital versatile disc (DVD), video capture device, touch screen, stylus, electro-acoustic transducer, microphone, speaker, etc. Input/output system 216 and I/O devices 218–222 may provide or receive analog or digital signals for communication between computer system 200 of the present invention and external devices, networks, or information sources. Input/output system 216 and I/O devices 218–222 preferably implement industry promulgated architecture standards, including Recommended Standard 232 (RS-232) promulgated by the Electrical Industries Association, Infrared Data Association (IrDA) standards, Ethernet IEEE 802 standards (e.g., IEEE 802.3 for broadband and baseband networks, IEEE 802.3z for Gigabit Ethernet, IEEE 802.4 for token passing bus networks, IEEE 802.5 for token ring networks, IEEE 802.6 for metropolitan area networks, 802.11 for wireless networks, and so on), Fibre Channel, digital subscriber line (DSL), asymmetric digital subscriber line (ASDL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on. It should be appreciated that modification or reconfiguration of computer system 200 of FIG. 2 by one having ordinary skill in the art would not depart from the scope or the spirit of the present invention. Thus, computer system 200 is just one of several computer systems capable of tangibly embodying electronic hybridization machine 116.

Figure 3:
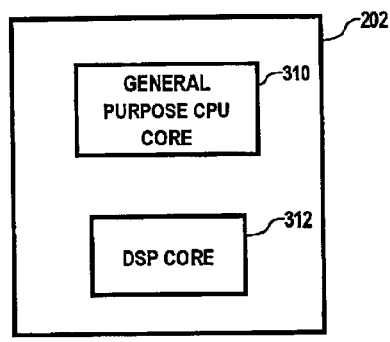
FIG. 3 is a block diagram of a digital signal processor (DSP) embodiment operable to embody the present invention where the DSP core and a general purpose central processing unit (CPU) are provided on a single chip.

Referring now to FIG. 3, an embodiment of a processor of a computer system embodiment of the present invention will be discussed. Processor 202 of computer system 200 in the embodiment shown of FIG. 3 may be configured to have two core components, a general purpose CPU core 310 and a digital signal processor core 312. General purpose core 310 may be utilized for general control functions to control the operation of the components of computer system 200 such as any of the components shown in or described with respect to FIG. 2. DSP core 312 may be utilized to implement digital signal processing algorithms so that the performance benefits of using a digital signal processor may be realized. It is noted that general purpose CPU core 310 and DSP core 312 of processor 202 may be implemented on a single integrate circuit or may each be implemented on separate integrated circuits. An example of a processor 202 as shown in the embodiment of FIG. 3 having a general purpose CPU core 310 and a DSP core 312 is described in U.S. Pat. No. 5,794,068. An example of such a suitable product to implement processor 202 is an ATHLON processor provided by Advanced Micro Devices, Inc. of Sunnyvale, Calif., where the ATHLON is a general purpose processor that includes DSP instructions for implementing DSP and communications extensions.

Figure 4:
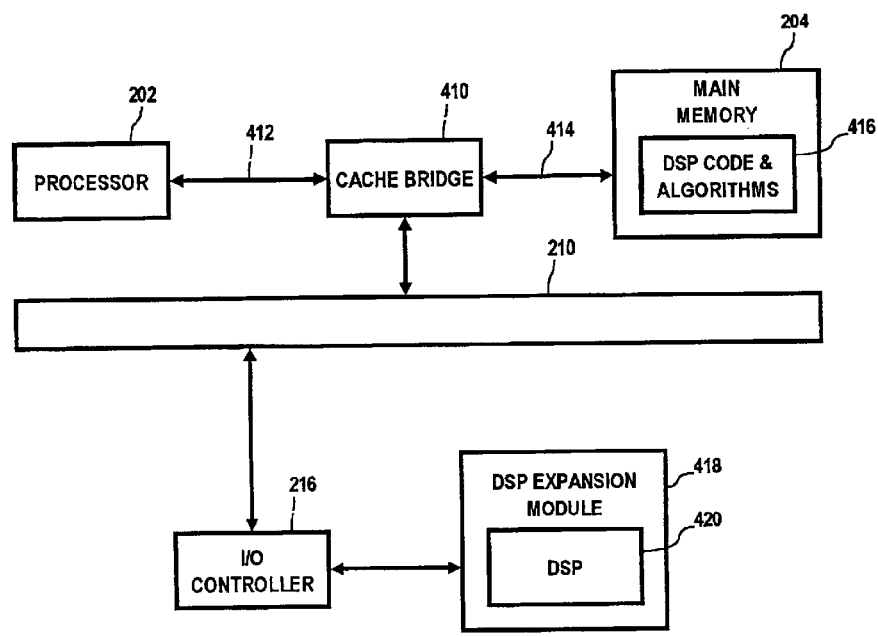
FIG. 4 is a block diagram of a computer appliance operable to embody the present invention that shows DSP code and algorithms executed by a processor of the computer appliance, and that further shows a DSP processor as an expansion module of the computer appliance in accordance with multiple embodiments of the present invention.

Referring now to FIG. 4, a block diagram of a system capable of implementing a digital signal processing routine in accordance with the present invention will be discussed. The system as shown in FIG. 4 illustrates how one or more embodiments of the present invention may be implemented using computer system 200 of FIG. 2. In one embodiment of the invention, processor 202 couples with main memory 204 via cache bridge 410. DSP code and algorithms 416 may be implemented in memory 204 and controlled and executed by processor 202. In this embodiment, DSP code & algorithms may be embodied as a program of instructions, such as computer software, that causes processor 202 to execute the steps of the algorithms of the present invention. In such an embodiment, processor 202 directly implements a digital signal processing routine. In an alternative embodiment, processor 202 emulates a DSP hardware processor in software. In a further alternative embodiment, a DSP expansion module 418 includes a DSP hardware processor 420 for executing digital signal processing algorithms including at least one or more algorithms for implementing an electronic hybridization assay in accordance with the present invention. DSP expansion module 418 couples with computer system 200 for example via I/O controller 216 which is in turn coupled with system bus 210. In an example embodiment, I/O controller 216 is a USB controller. As can be seen from FIG. 4, computer system 200 is capable of being configured to implement electronic hybridization machine 116 of FIG. 1, either in hardware, in software, or in a combination of hardware and software. Furthermore, electronic hybridization machine 116 may be entirely implemented in hardware using logic circuits without requiring the need for either a general purpose CPU processor or a digital signal processor. In such a hardware embodiment, electronic hybridization machine 116 may be implemented using combinational circuits, sequential circuits, or any combination thereof. An example of how a hardware circuit of this design may be implemented using shift registers is described in U.S. Pat. No. 3,670,151. It is noted that electronic hybridization assay machine 116 may include including at least one or more parallel channels for executing at least one or more correlation algorithms simultaneously, one correlation algorithm for each channel.

Figure 5:
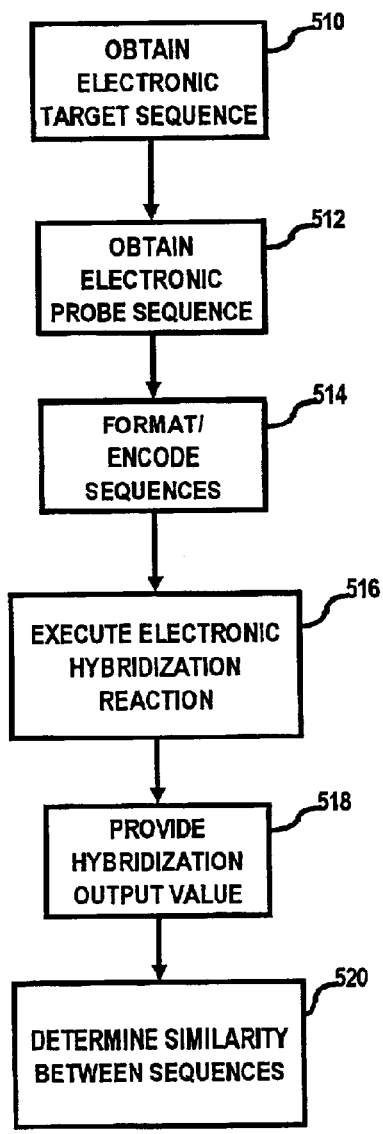
FIG. 5 is a flow diagram of a method for executing an electronic hybridization reaction in accordance with the present invention.

Referring now to FIG. 5, a flow diagram of a method for implementing an electronic hybridization assay in accordance with the present invention will be discussed. Electronic hybridization in accordance with the present invention is implemented by execution of method 500 by first sequencing the molecules of the assay to obtain the underlying sequence. An electronic target sequence is obtained at step 510, and an electronic probe sequence is obtained at step 512 using sequencing machines 112 and 120. Any candidate molecule need only at the very least be sequenced a single time. Once a molecule is sequenced, the sequence data may be stored in an electronic storage device such as storage device 126 or 128 for later retrieval. Thus, once a particular molecule, gene, or genome is sequenced, experimenters no longer need to perform assays in the physical and chemical domains since assays can be performed electronically in accordance with the present invention. In the event a candidate molecule has not already been sequenced or otherwise provided, it may be sequenced with sequencing machines such as sequencing machines 112 and 120 as known to those of skill in the sequencing art. The sequence data may be formatted or encoded at step 814 to optimize the results of an electronic hybridization algorithm executed by electronic hybridization machine 116. Formatting or encoding of the sequences is optionally performed since the output of typical sequencing machines may not be optimized for an electronic hybridization assay. For example, each residue, or subunit, of an oligonucleotide may be represented by the letter corresponding to the base of the residue, or subunit, typically in an American Standard Information Interchange (ASCII) coding scheme. Although an ASCII formatted output of a sequencing machine may be utilized by electronic hybridization machine 116, such text based codes are not optimized to implement faster processing algorithms such as the algorithms utilized by a DSP. Thus, the output of a typical sequencing machine may be encoded in a scheme that optimizes the efficiency of an electronic hybridization assay in accordance with the present invention. A sequence may be optimized in accordance with the present invention in one embodiment by electronically representing as a binary coded signal that uses a number of bits less than the number of bits used in a standard character set such as ASCII so that a subunit may be represented electronically with fewer bits than that typically used in a character set such as ASCII. In one particular embodiment, a sequence is optimized by encoding each subunit with less than seven bits. In another embodiment, a sequence is optimized by encoding each subunit with less than four bits. In yet another embodiment, a sequence is optimized by encoding each subunit with two bits. In yet a further embodiment, a sequence is optimized by encoding each subunit with only a single bit. As another mode for optimizing a sequence, a sequence is optimized by encoding at least one subunit with as a positive number, and encoding at least one other subunit with a negative number. It is not intended to limit the ways in which a sequence may be optimized in accordance with the present invention. Other types and combinations of optimization are contemplated. Optimizing a sequence for electronic sequence analysis in accordance with the present invention optimizes the electronic hybridization analysis executed by electronic hybridization machine in accordance with the present invention.

Figure 6:
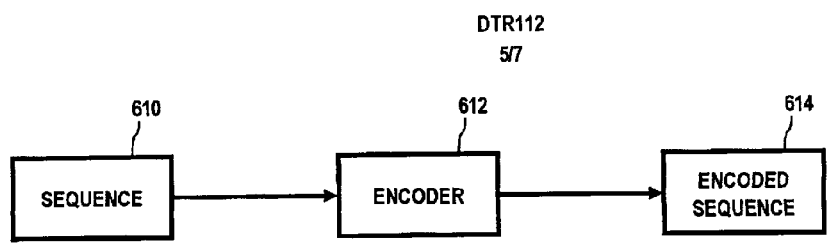
FIG. 6 is a block diagram of an encoder for encoding a sequence for utilization in an electronic hybridization reaction in accordance with the present invention.

As shown in FIG. 6, an electronic sequence 610 provided as an output from a sequencing machine is provided to an encoder 612 which provides an output sequence that is an encoded sequence 614 version of the electronic sequence 610. Encoded sequence 614 allows the oligonucleotide sequence to be represented using fewer bits than in a standard text encoded format such as ASCII, which typically requires 7 or 8 bits, thereby requiring less space in memory, for example. Furthermore, encoded sequence 614 allows for faster processing in an algorithm executed by electronic hybridization machine 116. Example encoding schemes in accordance with the preset invention are shown in the following table:

TABLE 1.1

Nucleotide Base Encoding Schema

| Nucleotide Base | Scheme 1 Decimal | Scheme 1 Binary | Scheme 2 Decimal | Scheme 2 Binary |
| --- | --- | --- | --- | --- |
| A | 1 | 001 | +1 | 001 |
| C | 2 | 010 | +2 | 010 |
| G | 3 | 011 | −1 | 101 |
| T or U | 4 | 100 | −2 | 110 |

Figure 7:
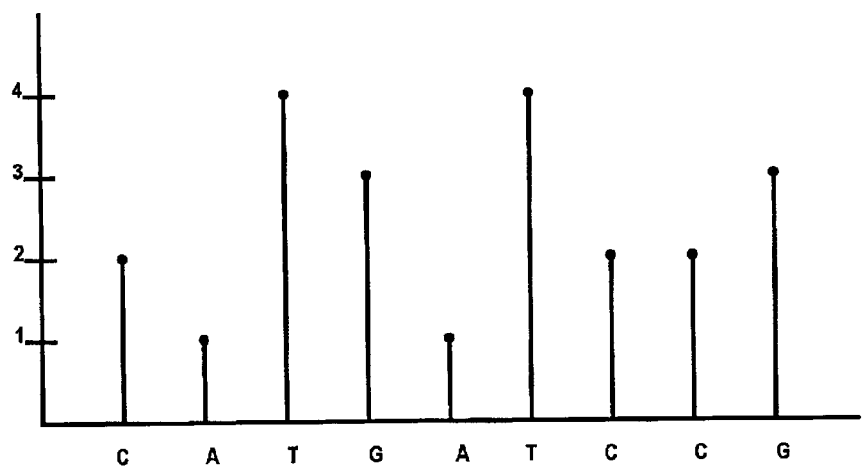
FIG. 7 is a graphical representation of one sequence encoding scheme in accordance with the present invention.
Figure 8:
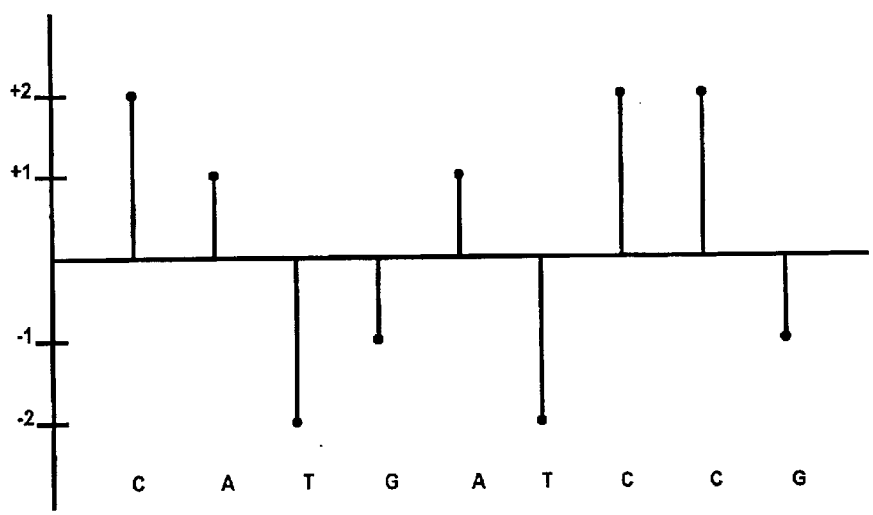
FIG. 8 is a graphical representation of another sequence encoding scheme in accordance with the present invention.

Coding Scheme 1 is graphically represented in FIG. 7, and example coding Scheme 2 is graphically represented in FIG. 8. Thus, in encoding Scheme 1, A is assigned a value of 1, C is assigned a value of 2, G is assigned a value of G, and T or U (depending on whether DNA or RNA is considered) is assigned a value of 4. It should be noted that the correspondence between bases and numerical values need not be limited to the order shown, and that alternative ordering may be utilized. In encoding Scheme 2, A is assigned a value of positive 1, C is assigned a value of positive 2, G is assigned a value of negative 1, and T or U is assigned a value of negative 2. As can be seen in FIGS. 7 and 8, when the coding schemes are used to plot the values of a given sequence, a waveform is defined. Although any coding scheme similar to either Scheme 1 or Scheme 2 may be utilized, an encoding scheme more like a Scheme 2 type encoding schemes is particularly suitable for optimizing a correlation algorithm implemented by electronic hybridization machine by optimally discriminating between sequences that are similar and sequences that are dissimilar. However, the present the invention need not be limited to the particular encoding schemes shown such that other combination and permutations of coding Scheme 1 or Scheme 2 may be utilized, or other types of coding schemes, for example a thermometer code, may be utilized without providing substantial change to the scope of the present invention.

After the optional execution of encoding step 514, electronic hybridization machine 116 executes an electronic hybridization reaction at step 516, which then allows the similarity between the two input sequences to be determined at step 520. The two sequences may represent a target sequence, for example the sequence of first molecule 1110, molecule A, and a probe sequence, for example the sequence of second molecule 118, molecule B. Hybridization output 124 represents the similarity between the two sequences. In one embodiment, hybridization output 124 is a numerical value or score that is proportional to or otherwise indicative of the similarity between the two sequences. In accordance with one embodiment of the present invention, electronic hybridization machine 116 implements a correlation signal processing algorithm to determine the similarity between the sequences wherein the correlation output is representative of the degree of similarity between the sequences. The correlation algorithm may be executed by a general purpose computer, hardware correlator device, or by a digital signal processor, comparator, etc., or a combination thereof.

In accordance with the present invention, the correlation algorithm is a mathematical operation that receives two sequences as an input and provides a correlation output value or sequence of values as an output. An objective in computing the correlation between two signals is to measure the degree to which the two signals are similar to thereby extract information on the relationship between the sequences. The information provided by a correlation algorithm is determined by the nature of the sequences and the context in which correlation algorithm is utilized. The correlation output sequence provides information that indicates the degree to which the two input sequences are similar, or as the case may be, identical. In accordance with the present invention, the sequences that represent the residues, or subunits, of the molecules to be analyzed are encoded as a discrete amplitude, discrete time-like signal as illustrated in FIGS. 7 and 8 and as shown in Table 1.1. Each subunit of the sequence is analogous to a discrete time unit. For example, a nucleotide molecule having 12 bases in its sequence is analogous to a discrete time signal having a length of 12 discrete time units. The discrete amplitude at each equivalent discrete time unit of the molecular sequence represents the identity of the corresponding subunit as shown and discussed with respect to FIGS. 7 and 8. Two molecule sequences x(n) and y(n) with the discrete time-like subunit variable, n, can be correlated using the following mathematical correlation algorithm:

$$r_{xy}(l) = \sum_{n=-\infty}^{\infty} x(n)y(n-l) \quad l = 0, \pm 1, \pm 2, \ldots$$

In the above equation, $r_{xy}(l)$ is the correlation result, itself a sequence of values, l is the shift, or lag, parameter, and n is the discrete time variable, which is the residue, or subunit, variable in the present invention. One way of describing the above correlation algorithm is that the sequence x(n) is left unshifted, and the sequence y(n) is shifted with respect to the sequence x(n) both in the negative direction and the positive direction by the shift parameter, l. Equivalently, the roles of sequences x and y could be reversed and the same result would be provided.

An example of a subroutine, written in FORTRAN programming language, for executing a correlation subroutine, is as follows:

```
SUBROUTINE CORRELATION (X, N, Y, M, R, LMAX)
DIMENSION X(1), Y(1), R(1)
DO 10 L = 1, LMAX
NL = M+1-L
IF (NL.GE.N-1) NL = N-1
R(L) = 0.0
DO 10 K = L, NL
R(L) = R(L)+X(K)*Y(K-L)
CONTINUE
END
```

In the correlation subroutine, above, X and Y are arrays having lengths N and M, respectively, and R is an array that contains the correlation result having a length of LMAX. In accordance with the present invention, electronic hybridization machine 116 implements a correlation algorithm to determine the extent to which two input sequences are similar.

In operation of the present invention, first molecule 110 has a sequence of N residues, and second molecule 118 has a sequence of M molecules. The molecules are sequenced by sequencing machines 112 and 120 respectively to provide sequence outputs 114 and 122. Electronic hybridization machine 116 encodes sequence outputs 114 and 122 such that first molecule 110 is represented by a sequence having N discrete subunits where each subunit has an amplitude that represents the corresponding identification of the subunit in a manner as shown in FIGS. 7 and 8. Likewise, second molecule 118 is represented by a sequence having M discrete subunits where each subunit has an amplitude that represents the corresponding identification of the subunit in a manner as shown in FIGS. 7 and 8. Electronic hybridization machine 116 executes a correlation algorithm on the two sequences and provides a hybridization output 124 which is a correlation output result value or sequence of values. The value or values of the correlation output result sequence determine the degree to which the input sequences are similar. The greater the value of the signal, the greater the degree to which the two input sequences are similar. A determination may be made whether two sequences are similar when a correlation output value exceeds a threshold value.

In an example where one sequence is larger than another, for example where the assay involves a probe sequence that represents a gene and a target sequence that represents a larger chromosome or genome, the position in the target sequence at which the similarity between the probe sequence and the target sequence exists is indicated in the correlation output result by the position of a maximum value of the correlation output sequence. Thus, in addition to an indication of the degree of similarity between two molecules as indicated by the value of the correlation output, an indication of the locus of similarity, or overlap, of two sequences can also be determined. This type of information may be particular useful, for example, in genetic mapping. This type of knowledge arises from the fact that in a correlation algorithm, one sequence is mathematically shifted with respect to the other sequence as the calculations are executed. Although a correlation algorithm is discussed as an example algorithm for executing an electronic hybridization assay in accordance with the present invention, the invention is not limited to any specific correlation algorithm. For example, any correlation algorithm or any algorithm similar to a correlation algorithm could also be utilized without providing substantial change to the scope of the present invention. For example, electronic hybridization machine 116 is capable of executing a correlation algorithm, a crosscorrelation algorithm, an autocorrelation algorithm, a convolution algorithm, a comparator algorithm, a Fourier transform, or a fast Fourier transform, discrete time or continuous time, or derivatives thereof such as a discrete cosine transform.

In one embodiment, electronic hybridization machine 116 implements a correlation algorithm as a program of instructions executed by processor 202 of computer system 200. Alternatively, electronic hybridization machine 116 implements a correlation algorithm via a hardware correlator device, for example using one or more shift registers, one or more comparators, one or more multivibrators, etc. such as described in U.S. Pat. No. 3,670,151. In a further embodiment, electronic hybridization machine 116 implements a correlation algorithm via digital signal processing techniques, and in particular, using a digital signal processor such as auxiliary processor 208 or DSP 420.

Advantages of utilizing a digital signal processor to implement a correlation algorithm may be understood upon an examination of digital signal processing. Digital signal processing algorithms typically involve repeatedly executing calculations having the general formula:

$$A=BC+D$$

The above equation, at the heart of the correlation algorithm discussed previously, involves a multiplication operation followed by an addition operation, a general purpose Complex Instruction Set Computer (CISC) or Reduced Instruction Set Computer (RISC) processor based computer (e.g., typical PC type computers) is not as efficient at implementing such an operation since these types of processors requires several clock cycles to execute. In contrast, digital signal processors (DSPs) are digital microprocessors having an architecture optimized to implement single cycle multiplication. A DSP has the multiplication function circuits internally hardwired so that a DSP can multiply two n-bit numbers in a single cycle. In addition, some DSP processors are further hardwired to execute an n-bit multiplication and a 2n-bit addition in a single clock cycle. A multiplication operation followed by an addition operation is known as a multiply-and-accumulate, which is represented by the A=BC+D calculation and which is central to a correlation algorithm. In contrast, a general purpose computer may require ten cycles to execute a multiplication and an additional cycle to execute an addition. Thus, digital signal processors are designed to optimally implement a correlation type algorithm in accordance with the present invention.

Figure 9:
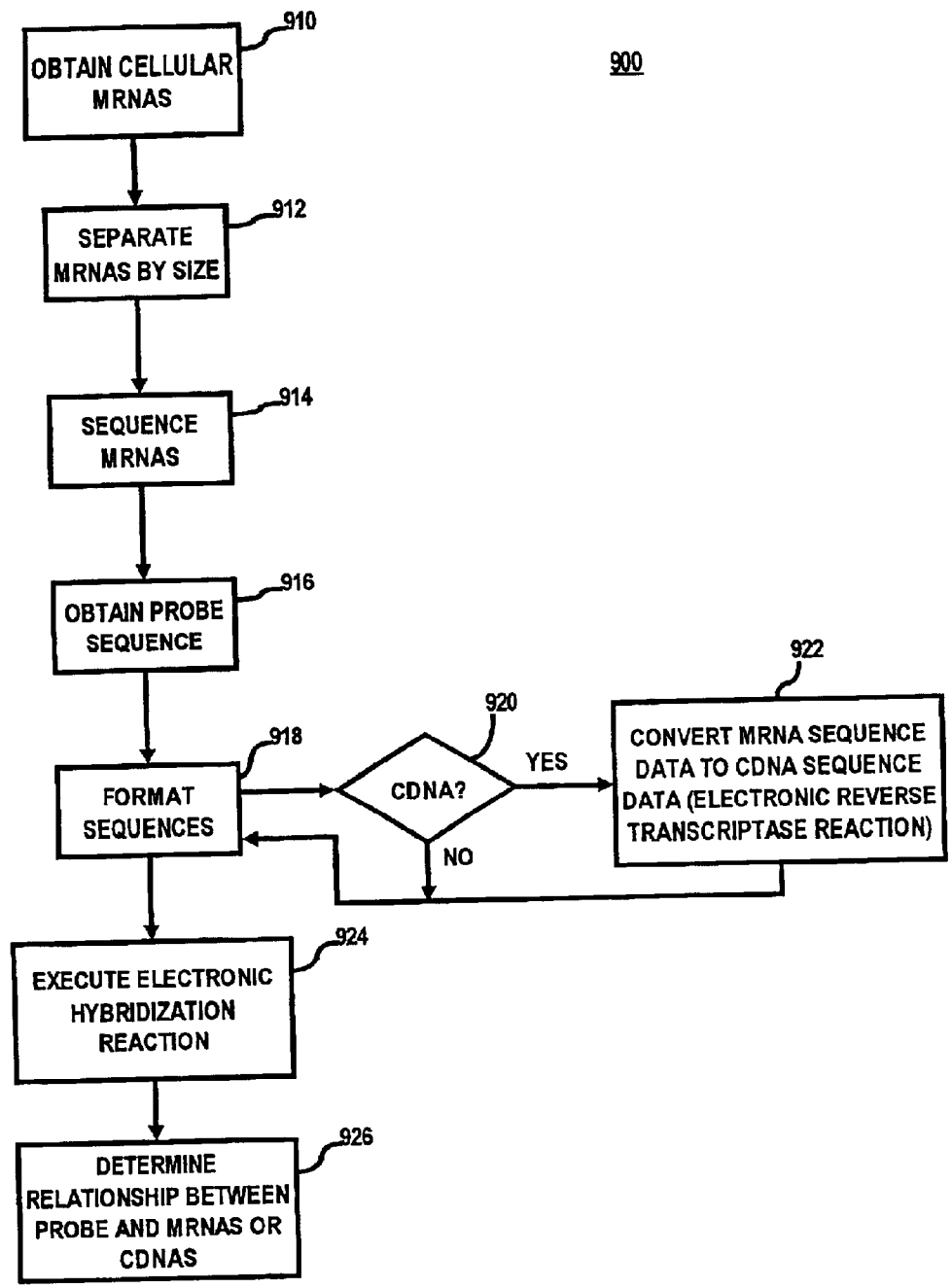
FIG. 9 is a flow diagram of a method for executing an electronic hybridization reaction in accordance with the present invention where RNA is utilized.

Referring now to FIG. 9, flow diagram of a method for executing an electronic hybridization assay using RNA will be discussed. Method 900 initiates with the obtaining of expressed cellular messenger RNAs (mRNAs) at step 910 from a host organism under examination. The mRNAs are separated by size at step 912, for example using electrophoresis through an agarose gel. The mRNAs are sequenced at step 914 using sequencing machine 112. Depending on the sequencing machine and sequencing techniques, step 912 may be optionally executed such that no separation is required before sequencing. A probe sequence may be selected and obtained at step 916, which may be optionally formatted or encoded in accordance with the present invention at step 918. If it is desirable to utilize complementary DNA (cDNA) sequences, as determined at step 920, then the mRNA probe sequence may be electronically converted to cDNA using an electronic reverse transcriptase reaction. This is executed by electronic hybridization machine 116, for example by converting uracil subunits to thymine subunits and converting the sequence to its complementary sequence. In any event, electronic hybridization machine 116 executes an electronic hybridization reaction at step 924 in accordance with the present invention with the thus obtained mRNA or cDNA sequence and reference sequence or target sequence. The relationship between the sequences is determined at step 926 by analyzing the resulting hybridization output 124, for example the correlation output sequence provided by a correlation algorithm. It is readily apparent that electronic hybridization machine 116 can be utilized to implement one or more types of assays by executing an algorithm in accordance with that described with respect to FIG. 9 such as an electronic expression level assay.

Figure 10:
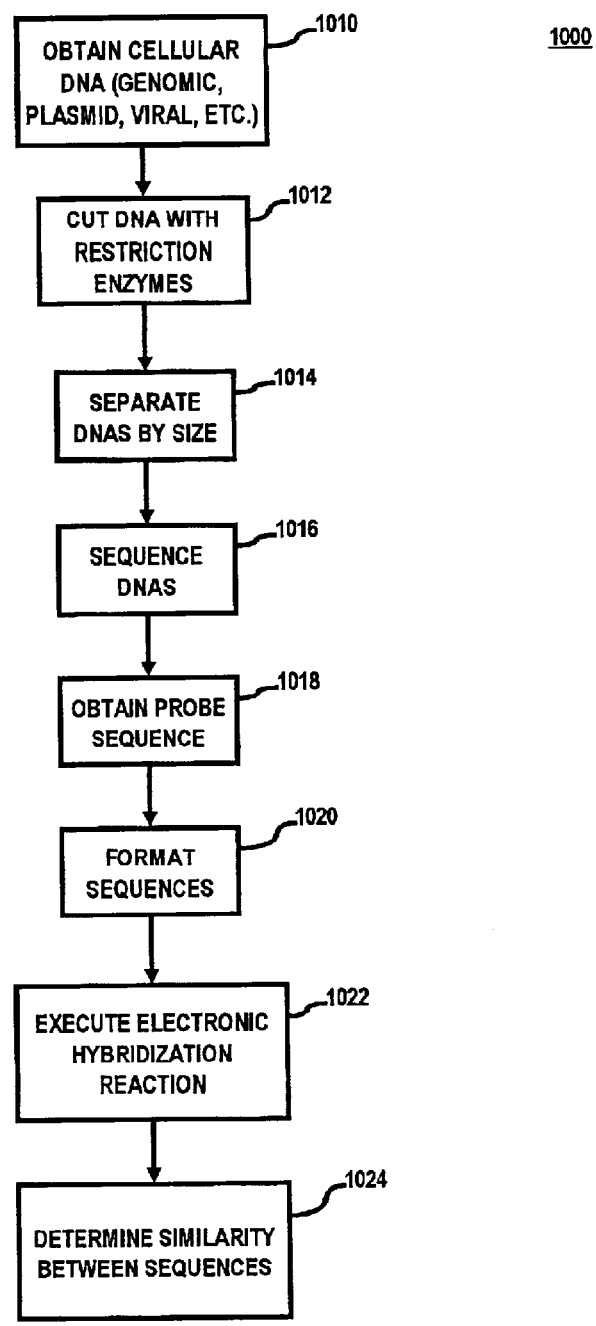
FIG. 10 is a flow diagram of a method for executing an electronic hybridization reaction in accordance with the present invention where DNA is utilized.

Referring now to FIG. 10, flow diagram of a method for executing an electronic hybridization assay using DNA will be discussed. Method 1000 initiates by obtaining cellular DNA at step 1010 from an appropriate organism or source such as genomic DNA from a cellular chromosome, plasmid, virus, etc. If necessary, the DNA is cut with one or more restriction enzymes to an appropriate length or lengths at step 1012. Optionally, 4 the DNA fragments are separated by size at step 1014, for example using electrophoresis through an agarose gel. The DNA is sequenced at step 1016 using sequencing machine 112 or 120, for example to obtain a sequence output 114 or 122, respectively, at step 1018. Optionally, the sequence output 114 or output 122 is formatted or encoded at step 1020. Electronic hybridization machine 116 executes an electronic hybridization reaction at step 1022 such that the similarity between the analyzed sequences can be determined at step 1024.

Although the invention has been described with a certain degree of particularity, it should be recognized that elements thereof may be altered by persons skilled in the art without departing from the spirit and scope of the invention. One of the embodiments of the invention can be implemented as sets of instructions resident in the main memory 204 of one or more computer systems configured generally as described in FIG. 2. Until required by the computer system, the set of instructions may be stored in another computer readable memory such as auxiliary memory 206 of FIG. 2, for example in a hard disk drive or in a removable memory such as an optical disk for utilization in a CD-ROM drive, a floppy disk for utilization in a floppy disk drive, a floppy-optical disk for utilization in a floppy-optical drive, or a personal computer memory card for utilization in a personal computer card slot. Further, the set of instructions can be stored in the memory of another computer and transmitted over a local area network or a wide area network, such as the Internet, when desired by the user. Additionally, the instructions may be transmitted over a network in the form of an applet (a program executed from within another application) or a servlet (an applet executed by a server) that is interpreted or compiled after transmission to the computer system rather than prior to transmission. One skilled in the art would appreciate that the physical storage of the sets of instructions or applets physically changes the medium upon which it is stored electrically, magnetically, chemically, physically, optically or holographically so that the medium carries computer readable information.

It is believed that the electronic hybridization assay and sequence analysis of the present invention and many of its attendant advantages will be understood by the forgoing description, and it will be apparent that various changes may be made in the form, construction and arrangement of the components thereof without departing from the scope and spirit of the invention or without sacrificing all of its material advantages, the form herein before described being merely an explanatory embodiment thereof. It is the intention of the following claims to encompass and include such changes.

What is claimed is:

1. A method, comprising:
   executing an electronic hybridization assay on a first sequence and a reference sequence, the first sequence representing at least one or more subunits of a first molecule and the reference sequence representing at least one or more subunits of a second molecule;
   providing an output representative of a hybridization reaction between the first and second molecules; and
   encoding the first sequence so that said executing step is optimized, wherein the first sequence includes at least one positive value and at least one negative value.

2. A method as claimed in claim 1, said executing step including the step of performing a correlation algorithm on the first sequence and the reference sequence, the output of said providing step including a correlation output.

3. A method as claimed in claim 1, further including the step of identifying a first molecule based upon the output of said providing step.

4. A method as claimed in claim 1, further including the step of identifying a position of sequence similarity between the first molecule and the second molecule.

5. An apparatus, comprising:
   means for executing an electronic hybridization assay on a first sequence and a reference sequence, the first sequence representing at least one or more subunits of a first molecule and the reference sequence representing at least one or more subunits of a second molecule;
   means for providing an output representative of a hybridization reaction between the first and second molecules; and
   means for encoding the first sequence so that execution by said executing means is optimized, wherein the first sequence includes at least one positive value and at least one negative value.

6. An apparatus as claimed in claim 5, said executing means comprising an electronic hybridization machine.

7. An apparatus as claimed in claim 5, said executing means comprising a computer appliance structure.

8. An apparatus as claimed in claim 5, said executing means comprising a digital signal processor structure.

9. An apparatus as claimed in claim 5, said executing means comprising a hardware correlator device structure.

10. An apparatus as claimed in claim 5, further comprising means for encoding the first sequence so that execution by said executing means is optimized.

11. An apparatus as claimed in claim 5, said executing means including means for performing a correlation algorithm on the first sequence and the reference sequence, the output of said providing means including a correlation output.

12. An apparatus as claimed in claim 5, further including means for identifying the first molecule based upon the output of said providing means.

13. An apparatus as claimed in claim 5, further including the means for identifying a position of sequence similarity between the first molecule and the second molecule.

14. A machine readable medium having a program of instructions stored thereon, the program of instructions for causing a machine to implement steps for executing an electronic hybridization assay according to the program of instructions, the steps comprising:
   executing an electronic hybridization assay on a first sequence and a reference sequence, the first sequence representing at least one or more subunits of a first molecule and the reference sequence representing at least one or more subunits of a second molecule;
   providing an output representative of a hybridization reaction between the first and second molecules; and
   encoding the first sequence so that said executing step is optimized, wherein the first sequence includes at least one positive value and at least one negative value.

15. A machine readable medium as claimed in claim 14, further comprising the step of encoding the first sequence so that said executing step is optimized.

16. A machine readable medium as claimed in claim 14, the executing step including the step of performing a correlation algorithm on the first sequence and the reference sequence, the output of said providing step including a correlation output.

* * * * *